United States Patent [19]
Liang et al.

[11] Patent Number: 5,486,539
[45] Date of Patent: Jan. 23, 1996

[54] METHOD OF USING PHENYLACETONITRILEALKYLAMINO-ALKYL-ORTHO-SUBSTITUTED ARYL COMPOUNDS AS IMMUNOSUPPRESSIVES

[75] Inventors: Chi-Dean Liang, Glenview, Ill.; John P. McKearn, Pacific; John M. Farah, Jr., St. Louis, both of Mo.; Richard A. Mueller, Glencoe, Ill.

[73] Assignee: G. D. Searle & Co., Chicago, Ill.

[21] Appl. No.: 204,121

[22] Filed: Mar. 1, 1994

Related U.S. Application Data

[63] Continuation of Ser. No. 926,732, Aug. 6, 1992, abandoned, which is a continuation of Ser. No. 623,596, Dec. 12, 1990, Pat. No. 5,162,569, which is a continuation-in-part of Ser. No. 609,145, Nov. 6, 1990, abandoned, which is a continuation of Ser. No. 456,004, Dec. 21, 1989, abandoned.

[51] Int. Cl.$^6$ ................................................ A61K 31/275
[52] U.S. Cl. ........................................... 514/521; 558/390
[58] Field of Search ............................ 558/390; 514/521

[56] References Cited

U.S. PATENT DOCUMENTS

| | | | |
|---|---|---|---|
| 3,261,859 | 7/1966 | Dengel | 260/465 |
| 4,438,131 | 3/1984 | Ehrmann et al. | 549/442 X |
| 4,593,042 | 6/1986 | Liang | 514/523 |
| 4,681,970 | 7/1987 | Liang | 558/408 |
| 5,162,569 | 11/1992 | Liang et al. | 560/42 |

OTHER PUBLICATIONS

Walz et al, *Transplantation*, 47; pp. 331–334 (1989).
Nel et al, *Scand. J. Immunology*, 24; pp. 283–290 (1986).
Chen et al, *Acta. Pharmacologica Sinica*, 11(3); pp. 281–285 (1989).

*Primary Examiner*—Joseph Paul Brust
*Attorney, Agent, or Firm*—J. Timothy Keane

[57] ABSTRACT

A class of substituted phenylacetonitrile-alkylaminoalkyl-ortho-substituted aryl compounds having immunosuppressive properties is described. Compounds of this class would be useful in reducing recipient rejection of transplanted organs and for treatment of autoimmune or inflammatory diseases. Compounds of particular interest are of the formula

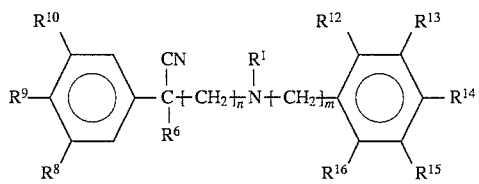

wherein m is one or two; wherein n is a number selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; with the proviso that at least one of $R^{12}$ and $R^{16}$ must be selected from hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; or a tautomer thereof or a pharmaceutically-acceptable salt thereof.

3 Claims, No Drawings

METHOD OF USING PHENYLACETONITRILEALKYLAMINO-ALKYL-ORTHO-SUBSTITUTED ARYL COMPOUNDS AS IMMUNOSUPPRESSIVES

RELATED APPLICATIONS

This is a continuation of U.S. application Ser. No. 07/926,732, filed Aug. 6, 1992, now abandoned; which in turn is a continuation of Ser. No. 07/623,596, filed Dec. 12, 1990, now U.S. Pat. No. 5,162,569; which in turn is a continuation-in-part of Ser. No. 07/609,145, filed Nov. 6, 1990, now abandoned; which in turn is a continuation of Ser. No. 07/456,004, filed Dec. 21, 1989, now abandoned.

FIELD OF THE INVENTION

This invention is in the field of clinical immunology and relates to compounds having immunosuppressive properties. Of particular interest is a family of phenylacetonitrilealkylaminoalkyl-o-substituted aryl compounds for reducing recipient rejection of transplanted organs, and for treatment of autoimmune or inflammatory diseases, allergic or asthmatic reactions and septic shock.

BACKGROUND OF THE INVENTION

Successful organ transplantation requires effective physiological and pharmacological intervention of the immune system of an organ recipient. Immunologic mechanisms are universal among the human species. But histocompatibility variations between donor and recipient lead inevitably to rejection of donor tissue by stimulation of the recipient's immune system except, perhaps, in donor-recipient pairing of the monozygotic type. One approach to intervention of immune response in an organ transplant recipient, especially a recipient targeted for an allogenic or homologous graft, is by the use of immunosuppressive drugs. These drugs have been used to prolong survival of transplanted organs in recipients in cases involving, for example, transplants of kidney, liver, heart, bone marrow and pancreas.

There are several types of immunosuppressive drugs available for use in reducing organ rejection in transplantation. Such drugs fall within three major classes, namely: antiproliferative agents, antiinflammatory-acting compounds and inhibitors of lymphocyte activation.

Examples of the class of antiproliferative agents are azathioprine, cyclophosphamide and methotrexate. The compound azathioprine acts by interrupting DNA synthesis through inhibition of purine metabolism. The compound cyclophosphamide is an alkylating agent which interferes with enzyme actions and nucleotide crosslinking. The compound methotrexate is a folic acid antagonist which interferes with nucleotide synthesis. While drugs of the antiproliferative class may be effective immunosuppressives in organ transplant recipients by limiting cell proliferation, these drugs which mediate mitosis and cell division have severe side effects on normal cell populations which have a high turn-over rate, such as bone marrow cells and cells of the gastrointestinal (GI) tract lining. Accordingly, such drugs often have severe side effects, particularly, bone marrow depression, liver damage, hair loss and GI tract disturbances.

A second class of immunosuppressive drugs for use in transplantation is provided by compounds having antiinflammatory action. Representatives of this drug class are generally known as adrenal corticosteroids and have the advantage of not exerting globally systemic cytotoxic effects. These compounds usually act by inhibiting T-cell proliferation, or by reducing IL-2 production, or by reducing chemotaxis, or by reducing neutrophil or macrophage activity. Typical examples of adrenal corticosteroids are prednisone and prednisolone. Compounds of this class are sometimes used in combination with cytotoxic agents, such as compounds of the antiproliferative class because the corticosteroids are significantly less toxic. But the adrenal corticosteroids lack specificity of effect and can exert a broad range of metabolic, antiinflammatory and auto-immune effects. Typical side effects of this class include increased organ-recipient infections and interference with wound healing, as well as disturbing hemodynamic balance, carbohydrate and bone metabolism and mineral regulation.

A third class of immunosuppressive drugs for use in organ transplantation is provided by compounds which generally prevent or inhibit lymphocyte activation. Such compounds usually act by blocking activated T-cell proliferation, or by inhibiting IL-2 production, or by inhibiting lymphokine production which depresses B-cell and macrophage actions. The cyclosporin family of compounds is the leading example of drugs in this class. Such compounds are fungal metabolites which have been found to be very effective in suppressing helper T cells so as to reduce both cellular and humoral responses to newly-encountered antigens. Cyclosporins alter macrophage and lymphocyte activity by reducing lymphokine secretion and, in particular, by interfering with activation of antigen-specific CD-4 cells, by preventing IL-2 secretion and secretion of many T-cell products, as well as by interfering with expression of receptors for these lymphokines. Cyclosporin A, in particular, has been used extensively as an immunosuppressor agent in organ transplantation. Other microbial metabolites include cyclosporins such as cyclosporin B and cyclosporin G, and another microbial product known as FK-506. Cyclosporin A suppresses humoral immunity as well as cell-mediated reactions. Cyclosporin A is indicated for organ rejection in kidney, liver, heart, pancreas, bone-marrow and heart-lung transplants. Cyclosporin A is also useful in the treatment of autoimmune and inflammatory diseases, including rheumatoid arthritis, Crohn's disease, Graves ophthalmopathy, severe psoriasis, aplastic anemia, multiple-sclerosis, alopecia areata, penphigus and penphigoid, dermatomyositis, polymyositis, Behcet's disease, uveitis, pulmonary sarcocidiosis, biliary cirrhosis, myasthenia gravis and atopic dermatitis.

Cyclosporins do possess several significant disadvantages. Firstly, while cyclosporins have provided significant benefits in organ transplantation, cyclosporins are non-specific immunosuppressives. Thus, immunologic reactions to transplanted tissue are not totally impeded, and desirable immune reactions may be reduced against other foreign antigens. Secondly, cyclosporins can produce severe side effects in many organ recipients. And cyclosporins show host-variable effects on the liver, the CNS and GI tract. Significant among the adverse side effects are damage to the kidney and hyperplasia of gum tissue.

Thus, the need remains for efficacious, selective immunosuppressive drugs in organ transplantation, especially for grafts between less-than-perfectly matched donor-recipient pairs.

Phenylacetonitrile compounds are known for use in treatment of cardiovascular diseases. For example, U.S. Pat. No. 3,261,859 describes phenylacetonitrile compounds, including the well-known compound verapamil, for use as coronary dilators. U.S. Pat. No. 4,593,042 describes certain bicycloamino-substituted phenylacetonitrilealkyl compounds, including several specific compounds having an isopropyl group attached to the alkylene alpha carbon of the phenylacetonitrile nucleus. Such compounds are characterized as calcium ion blockers for use in treatment of hypertension. U.S. Pat. No. 4,681,970 describes bicycloamino-substituted phenylacetonitrilealkyl compounds, several specific compounds of which have a long chain alkyl group (i.e., twelve carbons) attached to the alkylene alpha carbon of the phenylacetonitrile nucleus. These compounds are characterized as calcium channel blockers for treatment of hypertension.

Phenylacetonitrile compounds have been investigated for other pharmaceutical purposes. For example, certain calcium channel blocking agents, including verapamil, have been investigated for antiproliferative effects on T-cell mitogenesis [G. Walz et al, *Transplantation*, 47, 33–334 (1989)]. Various calcium channel blockers, including verapamil and nifedipine, have been studied for interaction with stimulated T-lymphocytes [A. Nell et al, Scan. J. Immunology, 24, 283–290 (1986)]. German Offen. 3826796 published 8 Feb. 1990 describes substituted phenylacetonitrile compounds for use in overcoming resistance to antimalarial or anticancer agents. The calcium antagonists verapamil, nifedipine and nicardipine were compared and found to produce dose-dependent acute and chronic antiinflammatory effects [W. R. Chen et al, *Acta. Pharmacologica Sinica*, 11 (3), 281–285 (1990) ].

DESCRIPTION OF INVENTION

Reduction in recipient rejection of a transplanted organ, or treatment of an autoimmune or inflammatory disease, or an allergic reaction or asthmatic condition, or treatment of septic shock may be accomplished by a method to suppress immune response in a recipient or treatment subject, which method comprises administering to the subject a therapeutically-effective amount of an immunosuppressive compound of Formula I:

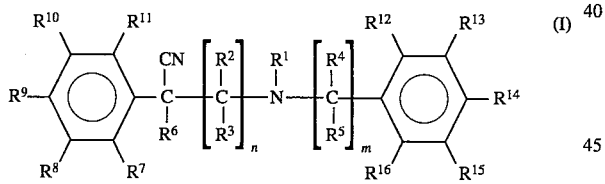

wherein m is one or two; wherein n is a number selected from one to ten, inclusive;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkylaryloxycarbonylalkyl, alkenyl, cycloalkenyl, aralkoxycarbonylalkyl, alkynyl, alkylthiocarbonylalkyl, alkylthiothiocarbonylalkyl, arylthiocarbonylalkyl, arylthiothiocarbonylalkyl, aralkylthiocarbonylalkyl, alkylarylthiocarbonylalkyl, alkylsulfonyl, aralkylsulfonyl and arylsulfonyl;

wherein each of $R^2$ and $R^3$ is independently selected from hydrido, alkyl, hydroxyalkyl, cycloalkyl, cycloalkylalkyl, aralkyl, aryl, aroyl, aryloxy, aryloxyalkyl, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkylthiocarbonyl, alkylthiocarbonyl, arylthiocarbonyl, arylthiothiocarbonyl, aralkylthiocarbonyl and alkylthiocarbonylalkyl;

wherein each of $R^4$, $R^5$ and $R^7$ through $R^{16}$ is independently selected from hydrido, hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonylalkyl, aralkylthiocarbonylthio, mercapto, alkylsulfinyl, alkylsulfonyl, aralkylsulfinyl, aralkylsulfonyl, arylsulfinyl, arylsulfonyl, and wherein each of $R^2$ through $R^5$ and $R^7$ through $R^{16}$ may be further independently selected from radicals of the formula

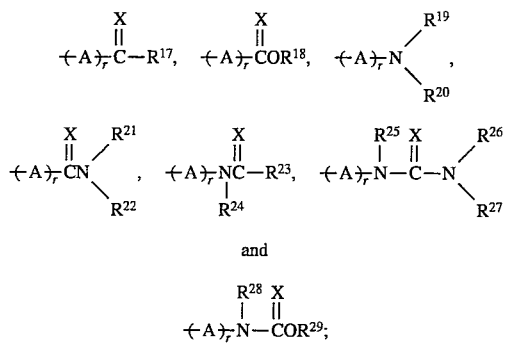

and

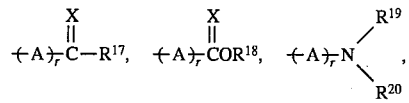

with the proviso that at least one of $R^{12}$ and $R^{16}$ must be selected from hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonylalkyl, aralkylthiocarbonylthio, mercapto, alkylsulfinyl, alkylsulfonyl, aralkylsulfinyl, aralkylsulfonyl, arylsulfinyl, arylsulfonyl, and radicals of the formula

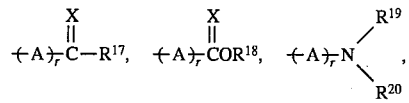

-continued

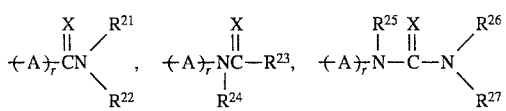

and

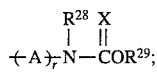

wherein A is selected from divalent alkyl, alkenyl and alkynyl groups; wherein X is oxygen atom or sulfur atom; wherein each r is a number independently selected from zero to six, inclusive; wherein each of $R^{17}$ through $R^{29}$ is independently selected from hydrido, alkyl, cycloalkyl, cycloalkylalkyl, aralkyl and aryl;

wherein $R^6$ is selected from hydrido, alkyl, hydroxyalkyl, cycloalkyl, cycloalkylalkyl, cycloalkyloxy, alkoxy, aralkyl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonylalkyl, aralkylthiocarbonylthio, alkylsulfinyl, alkylsulfonyl, aralkylsulfinyl, aralkylsulfonyl, arylsulfinyl and arylsulfonyl;

and wherein any of the foregoing A and $R^1$ through $R^{29}$ groups having a substitutable position may be substituted by one or more groups independently selected from alkyl, alkenyl, alkynyl, aralkyl, hydroxyalkyl, cyano, alkoxyalkyl, cycloalkyl, cycloalkylalkyl, aryl, aroylalkyl, cycloalkenyl, cyanoamino, alkylcarbonylalkyl, alkoxycarbonylalkyl, aralkoxycarbonylalkyl, carboxylalkyl, alkylthiocarbonylalkyl and alkylsulfonylalkyl;

or a tautomer thereof or a pharmaceutically-acceptable salt thereof.

A preferred class consists of compounds within Formula I wherein m is one or two; wherein n is a number selected from one to nine, inclusive;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkylaryloxycarbonylalkyl, alkenyl, cycloalkenyl, aralkoxycarbonylalkyl and alkynyl;

wherein each of $R^2$ and $R^3$ is independently selected from hydrido, alkyl, hydroxyalkyl, cycloalkyl, cycloalkylalkyl, aralkyl, aryl, aroyl, aryloxy, aryloxyalkyl, alkoxyalkyl, alkylcarbonylalkyl, alkenyl, cycloalkenyl, alkynyl, cyano, nitro, carboxyl, carboxyalkyl, alkylcarbonyloxyalkyl, alkoxycarbonylalkyl, aralkoxycarbonylalkyl, aralkylcarbonyloxyalkyl, mercaptocarbonyl, and mercaptoalkyl; wherein each of $R^4$, $R^5$ and $R^7$ through $R^{16}$ is independently selected from hydrido, hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, arylthio, mercapto, and wherein each of $R^2$ through $R^5$ and $R^7$ through $R^{16}$ may be further independently selected from radicals of the formula

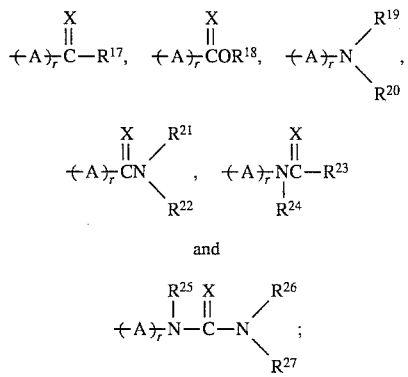

with the proviso that at least one of $R^{12}$ and $R^{16}$ must be selected from hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, arylthio, mercapto, and radicals of the formula

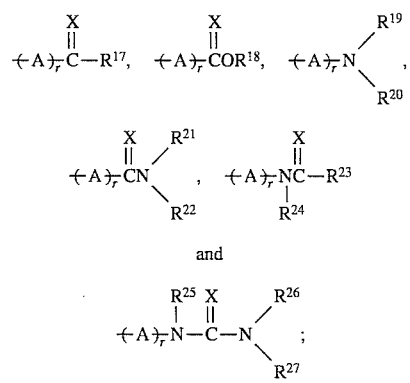

wherein A is selected from divalent alkyl, alkenyl and alkynyl groups; wherein X is oxygen atom or sulfur atom; wherein each r is a number independently selected from zero to five, inclusive; wherein each of $R^{17}$ through $R^{27}$ is independently selected from hydrido, alkyl, cycloalkyl, cycloalkylalkyl, aralkyl and aryl;

wherein $R^6$ is selected from hydrido, alkyl, hydroxyalkyl, cycloalkyl, cycloalkylalkyl, cycloalkyloxy, alkoxy, aralkyl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptoalkyl, alkoxycarbonyloxy, alkylthio, cycloalkylthio, and wherein any of the foregoing A and $R^1$ through $R^{27}$ groups having a substitutable position may be substituted by one or more groups independently selected from alkyl, alkenyl, alkynyl, aralkyl, hydroxyalkyl, cyano, alkoxyalkyl, cycloalkyl, cycloalkylalkyl, aryl, aroylalkyl, cycloalkenyl, cyanoamino, alkylcarbonylalkyl, alkoxycarbonylalkyl, aralkoxycarbonylalkyl and carboxylalkyl;

or a tautomer thereof or a pharmaceutically-acceptable salt thereof.

A more preferred class consists of compounds within Formula I wherein m is one or two; wherein n is a number selected from one to eight, inclusive;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkenyl and alkynyl, wherein each of $R^2$ and $R^3$ is independently selected from hydrido, alkyl, hydroxyalkyl, cycloalkyl, cycloalkylalkyl, aralkyl, aryl, aroyl, aryloxy, aryloxyalkyl, alkoxyalkyl, alkylcarbonylalkyl, alkenyl, alkynyl, cyano, nitro, carboxyl, carboxyalkyl, alkylcarbonyloxyalkyl and alkoxycarbonylalkyl,;

wherein each of $R^4$, $R^5$ and $R^7$ through $R^{16}$ is independently selected from hydrido, hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkoxycarbonyloxy, and wherein each of $R^2$ through $R^5$ and $R^7$ through $R^{16}$ may be further independently selected from radicals of the formula

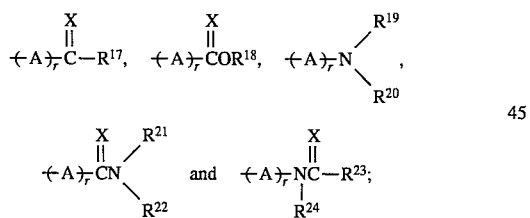

with the proviso that at least one of $R^{12}$ and $R^{16}$ must be selected from hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, and radicals of the formula

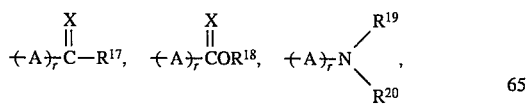

wherein A is selected from divalent alkyl, alkenyl and alkynyl groups; wherein X is oxygen atom or sulfur atom; wherein each r is a number independently selected from zero to four, inclusive; wherein each of $R^{17}$ through $R^{24}$ is independently selected from hydrido, alkyl, cycloalkyl, cycloalkylalkyl, aralkyl and aryl;

wherein $R^6$ is selected from hydrido, alkyl, hydroxyalkyl, cycloalkyl, cycloalkylalkyl, cycloalkyloxy, alkoxy, aralkyl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptoalkyl, and alkoxycarbonyloxy;

and wherein any of the foregoing A and $R^1$ through $R^{24}$ groups having a substitutable position may be substituted by one or more groups independently selected from alkyl, alkenyl, alkynyl, aralkyl, hydroxyalkyl, cyano, alkoxyalkyl, cycloalkyl, cycloalkylalkyl, aryl, aroylalkyl, cyanoamino, alkylcarbonylalkyl, alkoxycarbonylalkyl, aralkoxycarbonylalkyl and carboxylalkyl;

or a tautomer thereof or a pharmaceutically-acceptable salt thereof.

An even more preferred class consists of compounds within Formula I wherein m is one or two; wherein n is a number selected from one to seven, inclusive;

wherein $R^1$ is selected from hydrido, alkyl, hydroxyalkyl, cycloalkyl, cycloalkylalkyl, alkoxyalkyl, alkylcarbonylalkyl, alkoxycarbonylalkyl, alkenyl and alkynyl;

wherein each of $R^2$ and $R^3$ is independently selected from hydrido, alkyl, hydroxyalkyl, cycloalkyl, cycloalkylalkyl, phenylalkyl, phenyl, benzoyl, phenoxy, phenoxyalkyl, alkoxyalkyl, alkylcarbonylalkyl, alkenyl, alkynyl, carboxyl, carboxyalkyl, alkylcarbonyloxyalkyl and alkoxycarbonylalkyl;

wherein each of $R^4$ $R^5$ and $R^7$ through $R^{16}$ is independently selected from hydrido, hydroxy, alkyl, hydroxyalkyl, cycloalkyl, cycloalkylalkyl, cycloalkyloxy, alkoxy, phenylalkyl, phenyl, benzoyl, phenoxy, phenoxyalkyl, alkoxyalkyl, alkylcarbonylalkyl, alkynyl, carboxyl, carboxyalkyl, alkylcarbonyloxy, alkylcarbonyloxyalkyl, alkoxycarbonylalkyl, alkoxycarbonyloxy, and wherein each of $R^2$ through $R^5$ and $R^7$ through $R^{16}$ may be further independently selected from radicals of the formula

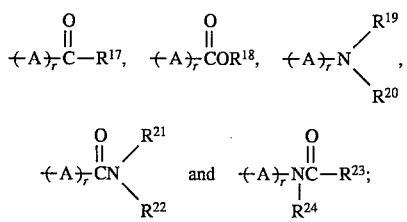

with the proviso that at least one of $R^{12}$ and $R^{16}$ must be selected from hydroxy, alkyl, hydroxyalkyl, cycloalkyl, cycloalkylalkyl, cycloalkyloxy, formyl, alkoxy, phenylalkyl, phenyl, benzoyl, phenoxy, phenoxyalkyl, phenalkoxy, alkoxyalkyl, alkylcarbonylalkyl, alkenyl, alkynyl, carboxyl, carboxyalkyl, alkylcarbonyloxy, alkylcarbonyloxyalkyl, alkoxycarbonylalkyl, alkoxycarbonyloxy, and radicals of the formula

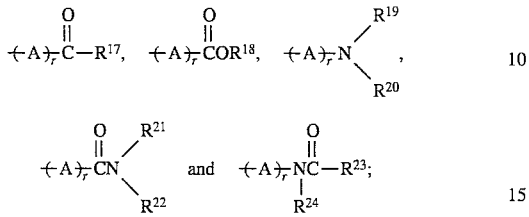

wherein A is selected from divalent alkyl, alkenyl and alkynyl groups; wherein each r is a number independently selected from zero to four, inclusive; wherein each of $R^{17}$ through $R^{24}$ is independently selected from hydrido, alkyl, cycloalkyl, cycloalkylalkyl, phenylalkyl and phenyl;

wherein $R^6$ is selected from hydrido, alkyl, hydroxyalkyl, cycloalkyl, cycloalkylalkyl, cycloalkyloxy, alkoxy, phenylalkyl, benzoyl, phenoxy, phenoxyalkyl, phenalkoxy, alkoxyalkyl, alkylcarbonyl, alkylcarbonylalkyl, alkoxycarbonyl, alkenyl, alkynyl, carboxyl, carboxyalkyl, alkylcarbonyloxy, alkylcarbonyloxyalkyl, alkoxycarbonylalkyl, mercaptoalkyl and alkoxycarbonyloxy; and wherein any of the foregoing A and $R^1$ through $R^{24}$ groups having a substitutable position may be substituted by one or more groups independently selected from alkyl, alkenyl, alkynyl, phenylalkyl, hydroxyalkyl, cyano, alkoxyalkyl, cycloalkyl, cycloalkylalkyl, phenyl, alkylcarbonylalkyl, alkoxycarbonylalkyl and carboxyalkyl;

or a tautomer thereof or a pharmaceutically-acceptable salt thereof.

An even more highly preferred class consists of compounds within Formula I selected from compounds of Formula II:

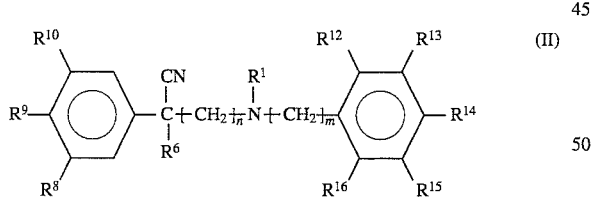

wherein m is one or two; wherein n is a number selected from one to six, inclusive; wherein $R^1$ is selected from hydrido, alkyl, hydroxyalkyl, cycloalkyl, cycloalkylalkyl, alkoxyalkyl, alkenyl and alkynyl;

wherein each of $R^8$, $R^9$, $R^{10}$ and $R^{12}$ through $R^{16}$ is independently selected from hydrido, hydroxy, alkyl, hydroxyalkyl, cycloalkyl, cycloalkylalkyl, cycloalkyloxy, alkoxy, phenoxy, benzyloxy, and radicals of the formula

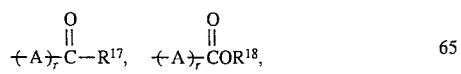

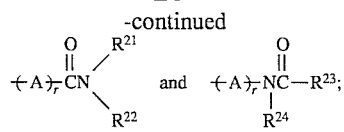

with the proviso that at least one of $R^{12}$ and $R^{16}$ must be selected from hydroxy, alkyl, hydroxyalkyl, cycloalkyl, cycloalkylalkyl, cycloalkyloxy, alkoxy, phenoxy, phenalkoxy, and radicals of the formula

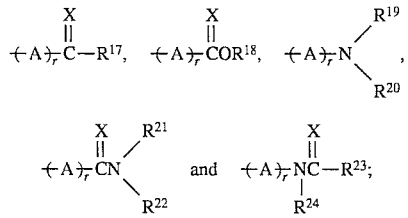

wherein A is a spacer group independently selected from one or more groups of the formula

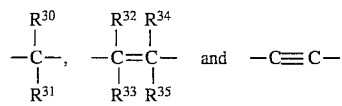

wherein each of $R^{30}$ and $R^{31}$ is independently selected from hydrido, alkyl, cycloalkyl, phenyl, benzyl, hydroxy, hydroxyalkyl, alkoxy, phenoxy, alkoxyalkyl, benzyloxy, cyano, alkanoyl,

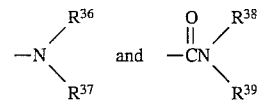

wherein each of $R^{36}$, $R^{37}$, $R^{38}$ and $R^{39}$ is independently selected from hydrido, alkyl and phenyl; wherein $R^{30}$ and $R^{31}$ may be taken together to form oxo or exomethylene; wherein each of $R^{32}$, $R^{33}$, $R^{34}$ and $R^{35}$ is independently selected from hydrido, alkyl, hydroxyalkyl and alkoxyalkyl;

wherein each of $R^{17}$, $R^{18}$, $R^{19}$, $R^{20}$, $R^{21}$, $R^{22}$, $R^{23}$ and $R^{24}$ is independently selected from hydrido, alkyl, cycloalkyl, cycloalkylalkyl and phenalkyl;

wherein each r is a number independently selected from zero to four, inclusive;

wherein $R^6$ is selected from hydrido, alkyl, hydroxyalkyl, cycloalkyl, cycloalkylalkyl, benzyl, alkenyl and alkynyl;

and wherein any of the foregoing A and $R^1$, $R^6$, $R^8$, $R^9$, $R^{10}$, $R^{12}$ through $R^{24}$ and $R^{30}$ through $R^{39}$ groups having a substitutable position may be substituted by one or more groups independently selected from alkyl, alkenyl, alkynyl, benzyl, hydroxyalkyl, alkoxyalkyl, cycloalkyl, cycloalkylalkyl and phenyl;

or a tautomer thereof or a pharmaceutically-acceptable salt thereof.

A more highly preferred class consists of compounds within Formula I wherein m is one or two; wherein n is a number selected from one to five, inclusive;

wherein $R^1$ is selected from hydrido, alkyl, hydroxyalkyl, alkoxyalkyl, alkenyl and alkynyl;

wherein each of $R^8$, $R^9$, $R^{10}$ and $R^{12}$ through $R^{16}$ is independently selected from hydrido, hydroxy, alkyl, hydroxyalkyl, alkoxy, and radicals of the formula

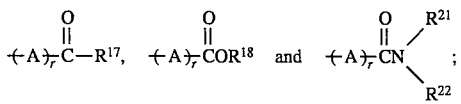

with the proviso that at least one of $R^{12}$ and $R^{16}$ must be selected from hydroxy, alkyl, hydroxyalkyl, alkoxy, and radicals of the formula

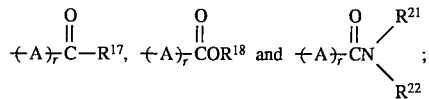

wherein A is a spacer group independently selected from one or more groups of the formula

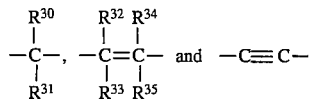

wherein each of $R^{30}$ and $R^{31}$ is independently selected from hydrido, alkyl, cycloalkyl, phenyl, benzyl, hydroxy, hydroxyalkyl, alkoxy and alkoxy and alkoxyalkyl;

wherein each of $R^{32}$, $R^{33}$, $R^{34}$ and $R^{35}$ is independently selected from hydrido, alkyl, hydroxyalkyl and alkoxyalkyl;

wherein each of $R^{17}$, $R^{18}$, $R^{21}$ and $R^{22}$ is independently selected from hydrido and alkyl;

wherein each r is a number independently selected from zero to four, inclusive;

wherein $R^6$ is selected from hydrido, alkyl, hydroxyalkyl, cycloalkyl, cycloalkylalkyl, benzyl, alkenyl and alkynyl;

and wherein any of the foregoing A and $R^1$, $R^6$, $R^8$, $R^9$, $R^{10}$, $R^{12}$ through $R^{18}$, $R^{21}$, $R^{22}$ and $R^{30}$ through $R^{35}$ groups having a substitutable position may be substituted by one or more groups independently selected from alkyl, alkenyl, alkynyl, hydroxyalkyl and alkoxyalkyl;

or a tautomer thereof or a pharmaceutically-acceptable salt thereof.

An even more highly preferred class consists of compounds within Formula II wherein m is one or two; wherein n is a number selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; with the proviso that at least one of $R^{12}$ and $R^{16}$ must be selected from hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; or a tautomer thereof or a pharmaceutically-acceptable salt thereof.

A family of compounds of specific interest within Formula I consists of the following compounds and pharmaceutically-acceptable salts thereof, as follows:

methyl 2-[2-[[4-cyano-4-(3,4-dimethoxyphenyl)-5-methylhexyl]methylamino]ethyl]-4,5-dimethoxybenzoate;

ethyl 2-[2-[[4-cyano-4-(3,4-dimethoxyphenyl)-5-methylhexyl]methylamino]ethyl]-4,5-dimethoxybenzoate;

n-propyl 2-[2-[[4-cyano-4-(3,4-dimethoxyphenyl)-5-methylhexyl]methylamino]ethyl]-4,5-dimethoxybenzoate;

n-butyl 2-[2-[[4-cyano-4-(3,4-dimethoxyphenyl)-5-methylhexyl]methylamino]ethyl]-4,5-dimethoxybenzoate;

n-hexyl 2-[2-[[4-cyano-4-(3,4-dimethoxyphenyl)-5-methylhexyl]methylamino]ethyl]-4,5-dimethoxybenzoate;

2-[2-[[4-cyano-4-(3,4-dimethoxyphenyl)-5-methylhexyl]methylamino]ethyl]-N-(1,1-dimethylethyl)-4,5-dimethoxybenzamide;

2-[2-[[4-cyano-4-(3,4-dimethoxyphenyl)-5-methylhexyl]methylamino]ethyl]-N-(1,1-dimethylethyl)-N-methyl-4,5-dimethoxybenzamide;

2-[2-[[4-cyano-4-(3,4-dimethoxyphenyl)-5-methylhexyl]methylamino]ethyl]-N-(1,1-dimethylethyl)-N-ethyl-4,5-dimethoxybenzamide;

2-[2-[[4-cyano-4-(3,4-dimethoxyphenyl)-5-methylhexyl]methylamino]ethyl]-N-(1,1-dimethylethyl)-N-propyl-4,5-dimethoxybenzamide;

2-[2-[[4-cyano-4-(3,4-dimethoxyphenyl)-5-methylhexyl]methylamino]ethyl]-N-(1,1-dimethylethyl)-N-butyl-4,5-dimethoxybenzamide;

2-[2-[[4-cyano-4-(3,4-dimethoxyphenyl)-5-methylhexyl]methylamino]ethyl]-N-(1,1-dimethylethyl)-N-pentyl-4,5-dimethoxybenzamide;

2-[2-[[4-cyano-4-(3,4-dimethoxyphenyl)-5-methylhexyl]methylamino]ethyl]-N-ethyl-4,5-dimethoxybenzamide;

2-[2-[[4-cyano-4-(3,4-dimethoxyphenyl)-5-methylhexyl]methylamino]ethyl]-N-methyl-4,5-dimethoxybenzamide;

2-[2-[[4-cyano-4-(3,4-dimethoxyphenyl)-5-methylhexyl]methylamino]ethyl]-N-propyl-4,5-dimethoxybenzamide;

2-[2-[[4-cyano-4-(3,4-dimethoxyphenyl)-5-methylhexyl]methylamino]ethyl]-N-butyl-4,5-dimethoxybenzamide;

2-[2-[[4-cyano-4-(3,4-dimethoxyphenyl)-5-methylhexyl]methylamino]ethyl]-N-pentyl-4,5-dimethoxybenzamide;

α-[3-[[2-(4,5-dimethoxy-2-methylphenyl)ethyl]methylamino]propyl]-3,4-dimethoxy-α-(1-methylethyl)benzeneacetonitrile;

α-[3-[[2-(4,5-dimethoxy-2-ethylphenyl)ethyl]methylamino]propyl]-3,4-dimethoxy-α-(1-methylethyl)benzeneacetonitrile;

α-[3-[[2-(4,5-dimethoxy-2-propylphenyl)ethyl]methylamino]propyl]-3,4-dimethoxy-α-(1-methylethyl)benzeneacetonitrile;

α-[3-[[2-(4,5-dimethoxy-2-butylphenyl)ethyl]methylamino]propyl]-3,4-dimethoxy-α-(1-methylethyl)benzeneacetonitrile;

α-[3-[[2-(4,5-dimethoxy-2-pentylphenyl)ethyl]methylamino]propyl]-3,4-dimethoxy-α-(1-methylethyl)benzeneacetonitrile;

α-[3-[[2-(4,5-dimethoxy-2-methylphenyl)ethyl]methylamino]propyl]-3,4,5-trimethoxy-α-(1-methylethyl)benzeneacetonitrile;

α-[3-[[2-(4,5-dimethoxy-2-ethylphenyl)ethyl]methylamino]propyl]-3,4,5-trimethoxy-α-(1methylethyl)benzeneacetonitrile;

α-[3-[[2-(4,5-dimethoxy-2-propylphenyl)ethyl]methylamino]propyl]-3,4,5-trimethoxy-α-(1-methylethyl)benzeneacetonitrile;

α-[3-[[2-(4,5-dimethoxy-2-butylphenyl)ethyl]methylamino]propyl]-3,4,5-trimethoxy-α-(1-methylethyl)benzeneacetonitrile;

α-[3-[[2-(4,5-dimethoxy-2-pentylphenyl)ethyl]methylamino]propyl]-3,4,5-trimethoxy-α-(1-methylethyl)benzeneacetonitrile;

α-[3-[[2-[4,5-dimethoxy-2-(3-oxo-1E-butenyl)phenyl]ethyl]methylamino]propyl]-3,4-dimethoxy-α-(1-methylethyl)benzeneacetonitrile;

α-[3-[[2-[4,5-dimethoxy-2-(3-oxo-1E-pentenyl)phenyl]
ethyl]methylamino]propyl]-3,4-dimethoxy-α-(1-methyl-
ethyl)benzeneacetonitrile;

α-[3-[[2-[4,5-dimethoxy-2-(3-oxo-1E-butanyl)phenyl]
ethyl]methylamino]propyl]-3,4-dimethoxy-α-(1-methyl-
ethyl)benzeneacetonitrile;

α-[3-[[2-[2-(hydroxymethyl)-4,5-dimethoxyphenyl]ethyl]
methylamino]propyl]-3,4-dimethoxy-α-(1-methylethyl-
)benzeneacetonitrile; and 1-methylethyl 2-[2-[[4-cyano-4-(3,4-dimethoxyphenyl)-5-
methylhexyl]methylamino]ethyl]-4,5-dimethoxyben-
zoate.

The term "hydrido" denotes a single hydrogen atom (H) . This hydrido group may be attached, for example, to a oxygen atom to form a hydroxyl group; or, as another example, two hydrido groups may be attached to a carbon atom to form a —CH$_2$— group. Where the term "alkyl" is used, either alone or within other terms such as "hydroxyalkyl", the term "alkyl" embraces linear or branched radicals having one to about twenty carbon atoms or, preferably, one to about fifteen carbon atoms. For some substituents, more preferred alkyl radicals are "lower alkyl", that is, radicals having one to about ten carbon atoms. For some substituents, most preferred alkyl radicals are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more preferred sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl, neopentyl, n-hexyl, n-heptyl, n-octyl, n-nonyl, n-decyl, n-undecyl, n-dodecyl, n-tridecyl, n-tetradecyl and n-hexadecyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

It is preferred that certain selections of radicals for $R^1$ be avoided. Radicals for $R^1$ which should preferably be avoided are alkyl, alkenyl and alkynyl moieties having a hydroxy, alkoxy or double or triple bond attached to the alpha carbon of the moiety, that is, the carbon attached to the nitrogen atom of Formula I on which $R^1$ is substituted. It is also preferred that certain selections of radicals for $R^6$ be avoided. Radicals for $R^4$ which should preferably be avoided are sulfhydryl, amino and mono-and di-substituted amino.

Also included in the family of compounds of Formulas I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases, including quaternary ammonium salts. The nature of the salt is not critical, provided that it is pharmaceutically-acceptable. Suitable pharmaceutically-acceptable acid addition salts of compounds of Formulas I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formulas I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

GENERAL SYNTHETIC PROCEDURES

Compounds embraced by Formula I may be prepared in accordance with Scheme I, which follows, wherein each of the R substituents are as defined in Formula I above, except where further noted.

Synthesis of the compounds of Formula I can be achieved by the reaction of bis-electrophile, sequentially, with two nucleophiles (Scheme I). The bis-electrophile can be, for example, an alkyl chain, substituted at the desired positions with a halogen or a sulfonic acid ester or the like or by a group that can be transformed into such an electrophile. It may be convenient, upon treatment with a nucleophile, that the two electrophilic groups have a differential reactivity toward nucleophilic substitution, e.g., a chloro group and a bromo group. Examples of bis-electrophiles are 3-bromochloropropane, 4-bromochlorobutane, 4-bromobutane-1-para-toluenesulfonate, 5-chloro-1-methyl-butane trifluoromethanesulfonate and the like. Examples of nucleophiles that can be reacted with the above bis-electrophiles are the anions of arylpropionitriles, prepared using non-nucleophilic bases, and primary or secondary amines. Non-nucleophilic bases are, for example, sodium hydride, potassium hydride, lithium di-iso-propyl amide (LDA, the salt of a sterically hindered amine) and the like. Electrophilic groups are indicated in Scheme I by $E_1$ and $E_2$.

SCHEME I

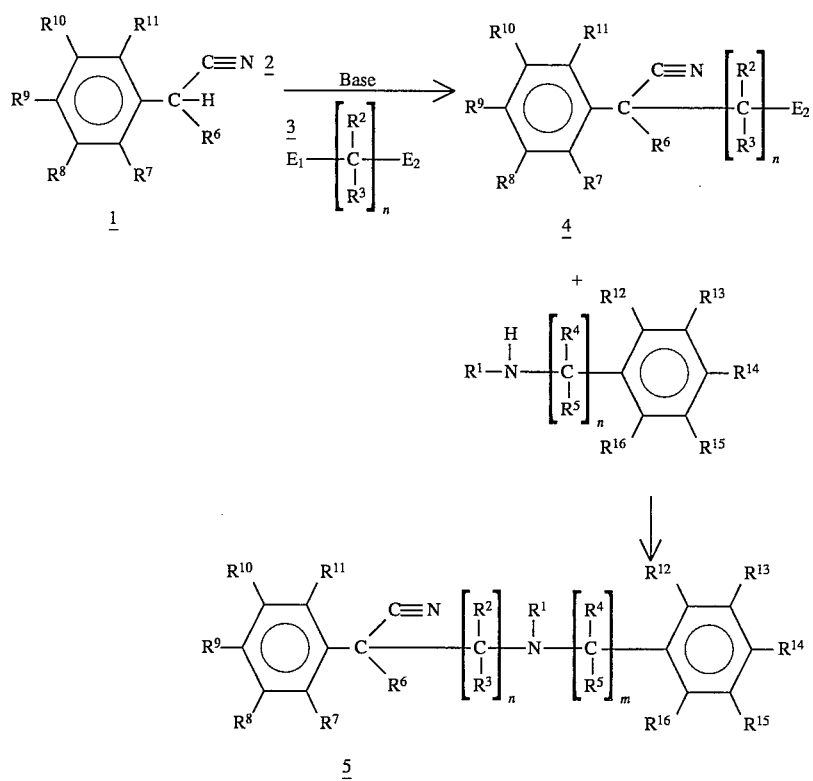

The following Examples 1–9 are detailed descriptions of the methods of preparation of compounds of Formula I. These detailed preparations fall within the scope of, and serve to exemplify, the above described Generic Procedures which form part of the invention. These Examples 1–9 are presented for illustrative purposes only and are not intended as a restriction on the scope of the invention. All parts are by weight unless otherwise indicated.

EXAMPLE 1

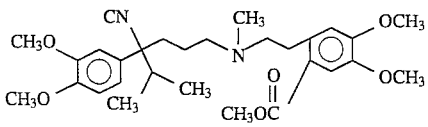

methyl 2-[2-[[4-cyano-4-(3,4-dimethoxyphenyl)-5-methyl-hexyl]methylamino]ethyl]-4,5-dimethoxybenzoate To verapamil (4.8 g) in 110 ml benzene was added 1 eq. of palladium acetate (2.6 g) and the mixture was stirred at r.t. for three days. This mixture was then transferred to a gasometric apparatus [R. F. Heck, *J.A.C.S.*, 83, 1097 (1961)] and flushed with carbon monoxide. To the mixture was then added methanol and after four hours 1.5 eq. triethylamine was added. The reaction mixture was filtered and the solvent was removed. The product was purified on a silica gel column and 2.2 g of product was obtained. [TLC: 5% MeOH/CHCl$_3$; R$_f$:0.45, Verapamil 0.5; C$_{29}$H$_{40}$N$_2$O$_6$; M.W. 512.65; structure was confirmed by $^1$HNMR; IR 1718 cm$^{-1}$]

|   | Calc'd. | Found |
|---|---------|-------|
| C | 67.95   | 67.01 |
| H | 7.86    | 8.12  |
| N | 5.46    | 5.24  |

EXAMPLE 2

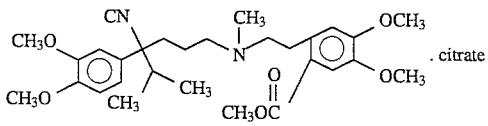

methyl 2-[2-[[4-cyano-4-(3,4-dimethoxyphenyl)-5-methyl-hexyl]methylamino]ethyl]-4.5-dimethoxybenzoate, 2-hydroxy-1,2,3-propanetricarboxylic acid salt A saturated solution of citric acid in ether was added dropwise to the product compound of Example 1 (300 mg) in 10 ml of ethyl ether until the resulting solution became slightly acidic. The resulting precipitate was filtered and was washed with 5 ml of ether twice. The precipitate when dried provided 402 mg of the title compound (95% yield) [m.p. 112°–117° C. dec.; C$_{35}$H$_{48}$N$_2$O$_{13}$; M.W. 704.77].

|   | Calc'd. | Found |
|---|---------|-------|
| C | 59.65   | 60.11 |
| H | 6.86    | 7.10  |
| N | 3.97    | 3.99  |

EXAMPLE 3

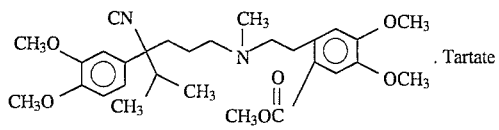

methyl 2-[2-[[4-cyano-4-(3,4-dimethoxyphenyl)-5-methyl-hexyl]methylamino]ethyl]-4,5-dimethoxybenzoate, 2,3-dihydroxybutanedioic acid salt;

To the product compound of Example 1 (500 mg) in 20 ml ethyl ether was added to a saturated solution of L-tartaric acid in ether until the resulting solution became slightly acid. The resulting precipitate was filtered and when dried yielded 0.6 g of the title compound [C$_{33}$H$_{46}$N$_2$O$_{12}$; M.W. 662.73].

|   | Calc'd. | Found |
|---|---------|-------|
| C | 59.81   | 60.35 |
| H | 7.00    | 7.01  |
| N | 4.23    | 4.33  |

EXAMPLE 4

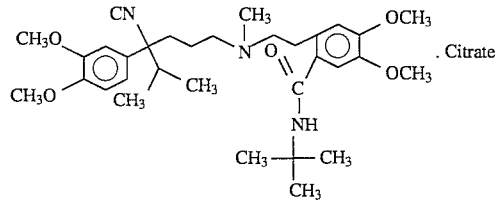

2-[2-[[4-cyano-4-(3,4-dimethoxyphenyl)-5-methylhexyl] methylamino]ethyl]-N-(1,1-dimethylethyl)-4,5-dimethoxy-benzamide, 2-hydroxy-1,2,3-propanetricarboxylic acid salt To verapamil (4.8 g in 110 ml benzene) was added 1 eq. of palladium acetate (2.6 g) . The mixture was stirred at r.t. for 3 days. The mixture was then transferred to a gasometric apparatus and flushed with carbon monoxide. To this mixture was then added t-butylamine. This mixture was stirred at r.t. for 4 hrs. The mixture was then filtered and solvent was removed. The product was purified on a silica gel column which provided 1.6 g (32% yield) [TLC: 40:60:2 EtOAc:toluene:Et$_3$N; R$_f$: Verapamil, 0.4; title compound, 0.3; IR: 1715$^{-1}$, 1640 cm$^{-1}$, 2210 cm$^{-1}$]. Then, a saturated solution of citric acid in ether was added to 1.2 g of the free base of the title compound in 20 ml ethyl ether until the resulting solution became slightly acidic. The precipitate was filtered and washed with ether to provide 1.6 g (98% yield) of title compound [m.p. 85°–115° C.; C$_{38}$H$_{55}$N$_3$O$_{12}$; structure was confirmed by $^1$HNMR].

|   | Cal'd. | Found |
|---|--------|-------|
| C | 61.2   | 62.72 |
| H | 7.38   | 7.46  |
| N | 5.63   | 6.08  |

EXAMPLE 5

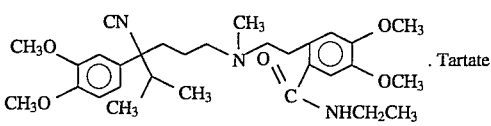

2-[2-[[4-cyano-4-(3,4-dimethoxyphenyl) -5-methylhexyl]methylamino]ethyl]-N-ethyl-4,5-dimethoxybenzamide, 2,3-dihydroxybutanedioic acid salt To verapamil (4.8g in 110 ml benzene) was added 1 eq. of palladium acetate (2.6 g). The mixture was stirred at r.t. for three days. The mixture was then transferred to a gasometric apparatus and flushed with carbon monoxide. To this mixture was then added ethylamine and the mixture was stirred for four hours. The mixture was filtered and organic solvent was removed [TLC: 40:60:2/SKB:EtOAc:Et$_3$N; Verapamil R$_f$ 0.25, Product 0.1]. This product compound was purified on a silica gel column and was obtained in 3.8 g 84% yield. The product compound (1.2 g) was dissolved in 40 ml ethyl ether and a saturated solution of L-tartaric acid was added until the resulting solution became slightly acidic. The precipitate, when filtered and dried, yielded 1.4 g of the title compound [structure was confirmed by $^1$HNMR].

|   | Cal'd. | Found |
|---|--------|-------|
| C | 60.43  | 61.01 |
| H | 7.31   | 7.42  |
| N | 6.22   | 6.29  |

EXAMPLE 6

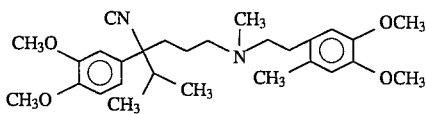

-[3-[[2-(4,5-dimethoxy-2-methylphenyl)ethyl]methylamino]propyl]-3,4-dimethoxy-α-(1-methylethyl)benzeneacetonitrile, 2,3-dihydroxybutanedioic acid salt To verapamil (4.8 g in 110 ml benzene) was added 1 eq. palladium acetate (2.6 g) and the mixture was stirred at r.t. for three days. Saturated aqueous NaCl (200 ml) and acetone (20 ml) were added to the reaction mixture which was stirred at r.t. for 15 min. The organic phase was separated and the aqueous phase was extracted with 50 ml CH$_2$Cl$_2$ three times. The organic phases were combined and the mixture was concentrated in vacuo to about 100 ml to remove water. To the mixture was then added 10.5 g of triphenylphosphine and the mixture was stirred at r.t. for one-half hour. Then, the mixture was cooled to 4° C., 15 mole (1.5 eq.) of methylmagnesiumchloride was added, the mixture was stirred at r.t. for one hour and then cooled to 4° C. To this mixture was added 10 ml of saturated aq. NH$_4$Cl solution dropwise. After one-half hour at r.t., the organic phase was separated and the resulting solid dried. The desired product was separated from verapamil by reverse phase column chromatography as follows:

Mobile Phase: 60-40 TEAA/CH$_3$CN Retention Time: Verapamil 9 min. title compound, 10.4 min. A yield of 25% (1.2 g) of the free base of the title compound was obtained. To the free base dissolved in 50 ml ethyl ester was added a saturated solution of tartaric acid in ether until the resulting solution was slightly acidic. The resulting precipitate was filtered and found to have the following analysis: [Calculated for C$_{28}$H$_{40}$N$_2$O$_4$.C$_4$H$_6$O$_6$.H$_2$O]

|   | Calculated | Found |
|---|------------|-------|
| C | 60.36      | 60.98 |
| H | 7.60       | 7.40  |
| N | 4.40       | 4.30  |

NMR(CD$_3$OD), δ(ppm); 0.78(d, 3H, J=6.6H$_z$), 1.22(d, 3H, J=6. 6Hz), 1.42(m,1H), 2.10–2.30(m, 4H), 2.18(S, 3H), 2.79(S, 3H), 2.8–3.3(m, 6H), 3.76(S, 6H), 3.80(S, 3H), 3.82(S, 3H), 6.73(S, 1H), 6.75(S, 1H), 6.92–7.1(m, 1H), $^{13}$CNMR(CD$_3$OD), δ(ppm); 18.8, 18.98, 19.4

EXAMPLE 7

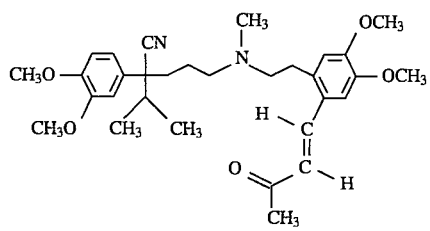

α-[3-[[2-4,5-dimethoxy-2-(3-oxo-1E-butenyl)phenyl]ethyl]methylamino]propyl]-3,4-dimethoxy-α-(1-methylethyl)benzeneacetonitrile To 4 g verapamil (8.8 mole) in 100 ml of benzene was added to 2.2 g of palladium acetate. The mixture was stirred for four days at room temperature. A saturated solution of NaCl in 100 ml of water and 96 ml of acetone was added to the resulting mixture, which was stirred at room temperature for 15 minutes. Solvent was then removed under reduced pressure. Then, there was added to the mixture 100 ml of toluene, 25 ml of triethylamine and 10 mmol of methylvinylketone. The mixture was heated at 120° C. for 2 hours, and then allowed to cool to room temperature. The organic phase was filtered, washed with water, dried, filtered again and solvent was removed. After separation by chromatography, the title compound was obtained (3.2 g, 80%) [m.p. 119–121, from ether].

|   | Calculated | Found |
|---|------------|-------|
| C | 71.24      | 71.57 |
| H | 8.10       | 8.30  |
| N | 5.36       | 5.25  |

NMR (ppm), 0.79(d, 3H, J=6.6H), 1.18(d, 3H, J=6.6H) 2.22(S, 3H), 2.36(S, 3H), 6.56(d, 1H, J=15H) 6.68(S, 1H), 6.80–6.92(m, 2H), 6.36(S, 1H) 7.08(S, 1H), 7.76(d, 1H, J=15H) 3.87(S, 3H), 3.88(S, 3H), 4.00(S, 3H), 4.01(S, 3H) IR 3410 cm$^{-1}$, 2150 cm$^{-1}$, 1659 cm$^{-1}$, 1639 cm$^{-1}$, 1509 cm$^{-1}$

EXAMPLE 8

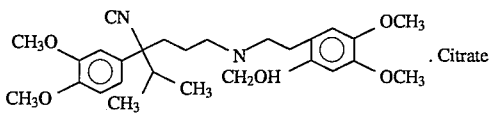

α-[3-[[2-[2-(hydroxymethyl)-4,5-dimethoxyphenyl]ethyl]methylamino]propyl]-3,4-dimethoxy-α-(1-methylethyl)

benzeneacetonitrile, 2-hydroxy-1,2,3-propanetricarboxylic acid salt

The compound of Example 1 (471 mg, 0.92 mmole) in 3 ml of ether was added to LiAlH$_4$ (21.3 mg, 56 mmole) dropwise during a 10 minute period. This mixture was stirred at r.t. for one-half hour. Five drops of H$_2$O was added to the mixture followed by the addition of five drops of 15% NaOH. Finally, 12 drops of H$_2$O was added to this mixture and the granular precipitate was filtered. The organic material was extracted with ethyl ether (30 ml) and was dried [TLC: 70:5:20/EtOAc: Et$_3$N:toluene; Example 1 compound, R$_f$ 0.5, free base of title compound, R$_f$ 0.2]. The free base of the title compound was separated and purified to provide 260 mg product (yield: 55%). This product compound was then dissolved in 10 ml ethyl ether, a saturated solution of citric acid was added, and then the precipitate was collected and dried [C$_{34}$H$_{48}$N$_2$O$_{12}$; the assigned structure was supported by NMR].

|   | Calculated | Found |
|---|---|---|
| C | 60.34 | 61.21 |
| H | 7.15 | 7.24 |
| N | 4.14 | 4.13 |

EXAMPLE 9

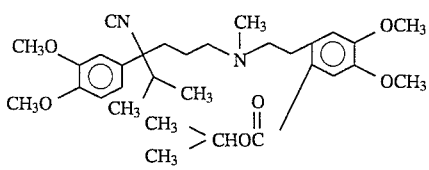

1-methylethyl 2-[2-[[4-cyano-4-(3,4-dimethoxyphenyl)-5-methylhexyl]methyl]amino]ethyl]-4,5-dimethoxybenzoate To verapamil (4.8 g in 110 ml benzene) was added 1 eq. of palladium acetate (2.6 g). This mixture was stirred at r.t. for 3 days arad then transferred to a gasometric apparatus and flushed with carbon monoxide. To this mixture was then added 1 eq. of isopropanol, and this mixture was stirred at r.t. for 4 hrs. Then, 1.5 eq. of triethylamine was added to the mixture, the resulting precipitate was filtered and the organic lager was concentrated to dryness. The product was purified on a silica gel column using CF$_3$CCl$_3$: isopropanol: NH$_4$OH/ 92.5:7:05 as eluent. The title compound was obtained as an oil [1.55 g, 60% yield, the structure was confirmed by $^1$HNMR analysis].

|   | Calculated | Found |
|---|---|---|
| C | 68.86 | 68.34 |
| H | 8.20 | 8.32 |
| N | 5.18 | 4.91 |

BIOLOGICAL EVALUATION

Assay A: Suppression of Mitogen-Stimulated Proliferation (Murine)

It is known that lymphocyte activation can be polyclonally stimulated by plant lectins and other mitogens that induce blast transformation and mitosis. Certain mitogens like Concanavalin A (ConA), preferentially activate T-lymphocytes. Exposure to ConA results in polyclonal activation of T-cells and can be used as an in vitro index for general immunomodulation of pan T-cell activity. In this assay spleen cells harvested from female Balb/c mice were incubated at 37° C., in 95% air/5% CO$_2$ atmosphere in 96 well microtiter plates (10$^5$ cells/well) for 5 days with Iscove's modified Dulbecco's medium [25 mM HEPES 2 mM L-glutamine, 5% fetal bovine serum and 2-mercaptoethanol (40 µM)](100 µl/well), concanavalin A (ConA) alone (Sigma, St. Louis, Mo.; 1.0 µg/ml) or ConA in the presence of test compounds (0.001–25 µM). Inhibition of ConA-stimulated proliferation was measured by colorimetric indicator of growth and proliferation, MTT (3-(4,5-dimethylthiazol-2-yl)-2 diphenyl tetrazolium bromide; (100 µl/well, 1 mg/ml) Sigma) [Mosmann, T., *J. of Immunological Methods*, 65, 55–63, 1988]. After four hours, plates were centrifuged (1200 rpm) media supernatants aspirated and dye loaded cells were solubilized in isopropanol (150 µl/well). The absorbance was measured on an ELISA plate reader with a test wavelength of 570 nm and a reference of 630 nm. The IC$_{50}$ values for active immunosuppressant compounds were calculated by four parameter logistic regression analysis of the results [Delean et al, *Am. J. Physiol.*, 235, 397 (1978)]. Results are shown in Table I.

Assay B: Suppression of Human Mitogen Stimulation Assay

Normal human donor peripheral blood mononuclear cells (PMNC) were isolated by density centrifugation using Ficoll-Paque(Pharacia LKB, Uppsala Sweden, 350 RCF 45 minutes). Cells were washed and incubated at 37° C. in 95% air/5% CO$_2$ atmosphere in 96 well microtiter plates (2×10$^5$ cells/well) for 96 hrs with RPMI 1640 medium containing 5% fetal bovine serum and 2-mercaptoethanol (40 µM), Phytohemagglutinin (Difco, Detroit, Mich. 10 µg/ml) in the presence or absence of test compounds. Inhibition of PHA stimulated proliferation was measured by reduced incorporation of $^3$H-thymidine (0.5 µCi/well, added during the last 24 hours of the assay). When possible, the IC$_{50}$ values for active immunosuppressant compounds were calculated by four parameter logistic regression analysis of the results [Delean et al, Id.]. Results are shown in Table I.

Assay C: One-Way Mixed Lymphocyte Reaction (Human)

The mixed lymphocyte reaction (MLR) is an assay that measures T-cell blast cell transformation and mitosis which occurs when lymphocytes from different major and minor histocompatibility complex (MHC) haplotypes are cocultured. This response is considered a "one-way MLR" when stimulator cells are made unresponsive by inhibition of DNA synthesis (treatment with mitomycin-C or gamma-irradiation) prior to coculture with responder cells. This assay can be used as an indicator of the cellular immunomodulation mechanisms involved in transplant rejection. In this assay, human peripheral blood mononuclear cells (PMNC) were used as the responder cell population and were isolated from normal donor blood as follows: Blood samples were collected in LeucoPREP™ tubes (Becton Dickinson, Lincoln Park, N.J.) and the mononuclear cell preparation was obtained by following the manufacturers procedures. Isolated mononuclear cells were co-incubated at 6×10$^4$ cells/well with a stimulator cell line at 2×10$^4$ cells/well in RPMI 1640 medium containing 5% fetal bovine serum and 2-mercaptoethanol (40 µM). The stimulator cell line, Rail, which was derived from a human Burkitt lymphoma (American Type Culture Collection, Rockville Md.) was previously inactivated by mitomycin-C treatment (Sigma, St. Louis Mo., 25 µg/ml, 37° for 30 minutes). After repeated washings of mitomycin-C from the stimulator cell line, cocultures were incubated in 96 well microtiter plates at 37° C., in 95% air/5% CO$_2$ atmosphere for 120 hours in the presence or absence of test compounds (0.1–25 µM). Inhibition of proliferation was measured by reduced incorporation of $^3$H-thymidine (0.5 μCi/well, added during the last 24 hours of the assay). The IC$_{50}$ values for the immunosuppressant compounds were calculated by four parameter logistic regression analysis of the results [Delean et al, Id.] Results are shown in Table I.

TABLE I

In Vitro Suppression of Immune Response

| Test Compound of Example # | Assay A[1] IC$_{50}$ μM | Assay B[2] IC$_{50}$ (μM) | Assay C[3] IC$_{50}$ (μM) |
|---|---|---|---|
| 1 | NT | NT | NT |
| 2 | 7.1 | 5.4 | 4.3 |
| 3 | 8.7 | 5.3 | NT |
| 4 | 13.3 | 9.9 | 8.9 |
| 5 | >25 | >25 | 20.2 |
| 6 | NT | NT | NT |
| 7 | 7.9 | NT | 15.5 |
| 8 | NT | NT | NT |
| 9 | NT | NT | NT |

NT = Not Tested
[1]Assay A: Suppression of Mitogen-Stimulated Proliferation (Murine)
[2]Assay B: Suppression of Human Mitogen Stimulation
[3]Assay C: One-Way Mixed Lymphocyte Reaction (Human)

Assay D: Calcium Flux Assay

One of the earliest requirements of lymphocyte activation involves the rapid mobilization of intracellular calcium and the sustained influx of extracellular calcium. These cellular responses to lymphocyte activators can be measured by calcium-binding fluorescent dyes such as Indo-1 [P. S. Rabinovitch, et al *J. Immunol, b 137*, 952 (1986)]. The rapid and sustained changes in intracellular calcium can be used to discriminate classes of immunomodulatory compounds which alter early events in lymphocyte activation. Human mononuclear cells or the human Jurkat T-cell line (ATCC, Rockville Md.) were loaded with the calcium-sensitive dye, Indo-1 (5 μM), washed and incubated for 2–5 minutes in the presence or absence of test compounds. Calcium flux was initiated in lymphocytes by the binding of crosslinked antibody to the T cell receptor (αCD3 at 250 ng/ml followed by goat-anti-mouse IgG) or the lectin Phytohemagglutinin (PHA, 100 ug/ml). Jurkat cell activation was initiated by the addition of purified antibody to the T cell receptor (αCD3, 250 ng/ml). Subsequent changes in the concentration if intracellular calcium was monitored over time (6 min) by flow cytometry (Epics 753, Coulter Electronics, Hialeah Fla.) to determine modulation of the initial calcium-mediated activation of the cells [P. S. Rabinovitch, et al, Id.]. Jurkat cells were incubated in the presence of compounds of Ex. #2, #4 and #5 at 1 to 10 times the IC$_{50}$ values of Assay A listed in Table I for 5 minutes prior to flow cytometry. Tested compounds within this group inhibited the plateau phase of intracellular calcium levels induced by stimulation at 5 to 10 times the IC$_{50}$ values of Assay A. Human mononuclear cells were incubated in the presence of the compound of Ex. #2, #4 and #5 at 2×, 5× and 10× values of Assay A the IC$_{50}$ listed in Table I. The compounds of Ex. #2, #4 and #5 inhibited calcium flux in a dose dependent manner.

Assay E: Combinations of Invention Compound with Cyclosporin A (CsA) in Inhibiting Mitogen Induced T-cell Proliferation PHA stimulated PBM cells were cultured in a constant dose of a compound of Formula I and with decreasing doses of CsA, starting with the minimum dose of CsA that totally blocks proliferation (125 ng/ml). CsA doses as low as 6 ng/ml were utilized. The concentration of the compound of Example #3 was kept constant at 5 uM, whereas the concentrations of the compounds of Example #4 and Example #5 were kept at 25 uM. Synergism was evidenced by a super-additive inhibition of the mitogen-induced T-cell proliferation, by the antiproliferative effects mediated by CsA and the compounds of the present invention. Addition of the compounds of Formula I shifted the IC$_{50}$ of CsA by 3 to 4-fold.

Assay F: Calcium Antagonist Effects

An excised aortic segment was mounted in a tissue bath containing modified Krebs solution. After depolarization of the tissue with K$^+$ (100 mM), Ca$^{++}$, in cumulative concentrations of $10^{-3}$M, $3.2 \times 10^{-3}$M and $10^{-2}$M, was injected into the bath to produce vascular smooth muscle contraction. The developed tension (g) was measured and control dose-response values are obtained. After 1 hr incubation with a test compound at $10^{-6}$M concentration, the same doses of Ca$^{++}$ are repeated. The log dose-response curves of control and after treatment were analyzed by linear regression.

| Compound Example # | pA$_2$ |
|---|---|
| 1 | 6.81 |
| 4 | 6.56 |

Assay G: Calcium Channel Blocker Effects

Under ether anesthesia, the jugular vein, femoral artery and left ventricle of adult male SHR were cannulated. After a 3–5 hour recovery period, animals ere treated with either test compound or placebo. Ten minutes was allowed for steady state conditions to be reached. Arterial pressure was then monitored via the femoral cannula. Immediately after this measurement, the reference blood sample was taken and radioactively-labeled microspheres were injected into the left ventricle. Rats were then sacrificed; organs were removed, weighed and counted. Cardiac output was computed. Percent cardiac output distribution per gram tissue, flow per gram tissue, and resistance times gram tissue were calculated from the following organs: brain, heart, kidneys, splanchnic organs (liver plus pancreas, spleen and G. I. tract), skeletal muscle and skill. The tested compound was administered as an I.V. bolus of 1.0 mg/kg. Differences in mean values between treatment and control groups were analyzed by a one-way one variable analysis and least significant difference test. The Example #6 compound caused a decrease of vascular resistance as follows:

In the brain:

| | |
|---|---|
| Compound Example #6 | 149 mm Hg min. g/ml |
| Control (DMSO) | 240 mm Hg min. g/ml |
| $p < 1.05$ | |
| In the kidneys: | |
| Compound Example #6 | 22.4 mm Hg min. g/ml |
| Control (DMSO) | 37.6 mm Hg min. g/ml |
| $p < 0.05$ | |

Assay H: Blood Pressure Reducing Effects

Systemic blood pressure effects were assessed in an anesthetized spontaneously hypertensive rat. The test compound was administered intragastrically at $10^{-3}$M. Initial mean arterial blood pressure (MAP) was measured directly via a previously implanted arterial catheter immediately before administration of the compound. Blood pressure readings were made 1, 2, 3, and 4 hours after administration of the test compound.

| Compound Example # | Decrease in MAP (mm Hg) |
|---|---|
| 4 | 18 |

| Compound Example # | Decrease in MAP (mm Hg) |
|---|---|
| 5 | 20 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered to a mammalian subject, such as a human subject, by any suitable route, preferably in the form of a pharmaceutical composition adapted to such a route, and in a dose effective for the treatment intended. Therapeutically-effective doses of the compounds of the present invention required to prevent or arrest the progress of the medical condition are readily ascertained by one of ordinary skill in the art. The compounds and composition may, for example, be administered by various routes including oral, nasal, topical, buccal and sublingual, or by parenteral administration such as subcutaneous, intramuscular, intravenous and intradermal routes.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to suppress immune response in a subject, said method comprising administering to said subject a therapeutically-effective amount of an immunosuppressive compound of Formula I:

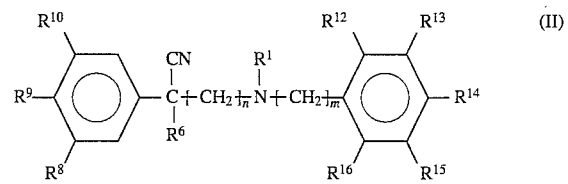

wherein m is one or two; wherein n is a number selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkoxy, alkenyl, alkynyl, alkylcarbonyl, alkoxycarbonyl and alkoxyalkyl; with the proviso that at least one of $R^{12}$ and $R^{16}$ must be selected from alkoxycarbonyl; or a tautomer thereof or a pharmaceutically-acceptable salt thereof.

2. The method of claim 1 wherein said immunosuppressant compound is selected from compounds and their pharmaceutically-acceptable salts of the group consisting of methyl 2-[2-[[4-cyano-4-(3,4-dimethoxyphenyl)-5-methylhexyl]methylamino]ethyl]-4,5-dimethoxybenzoate;

ethyl 2-[2-[[4-cyano-4-(3,4-dimethoxyphenyl)-5-methylhexyl]methylamino]ethyl]-4,5-dimethoxybenzoate;

n-propyl 2-[2-[[4-cyano-4-(3,4-dimethoxyphenyl)-5-methylhexyl]methylamino]ethyl]-4,5-dimethoxybenzoate;

n-butyl 2-[2-[[4-cyano-4-(3,4-dimethoxyphenyl)-5-methylhexyl]methylamino]ethyl]-4,5-dimethoxybenzoate;

n-hexyl 2-[2-[[4-cyano-4-(3,4-dimethoxyphenyl)-5-methylhexyl]methylamino]ethyl]-4,5-dimethoxybenzoate; and 1-methylethyl 2-[2-[[4-cyano-4-(3,4-dimethoxyphenyl)-5-methylhexyl]methylamino]-4,5-dimethoxybenzoate.

3. The method of claim 1 further characterized by suppressing immune response in a subject to prevent rejection of an organ transplanted to said subject.

* * * * *